(12) United States Patent
Mohorovic et al.

(10) Patent No.: US 12,290,830 B2
(45) Date of Patent: May 6, 2025

(54) PERFUME DOSING DEVICE

(71) Applicant: M33 d.o.o., Ljubljana-Sentvid (SI)

(72) Inventors: Simon Mohorovic, Dobrova (SI); Marko Matijevic, Ljubljana (SI)

(73) Assignee: M33 d.o.o., Ljubljana-Sentvid (SI)

( * ) Notice: Subject to any disclaimer, the term of this patent is extended or adjusted under 35 U.S.C. 154(b) by 166 days.

(21) Appl. No.: 17/763,743

(22) PCT Filed: Aug. 21, 2020

(86) PCT No.: PCT/SI2020/050020
§ 371 (c)(1),
(2) Date: Mar. 25, 2022

(87) PCT Pub. No.: WO2021/061056
PCT Pub. Date: Apr. 1, 2021

(65) Prior Publication Data
US 2022/0339650 A1    Oct. 27, 2022

(30) Foreign Application Priority Data

Sep. 27, 2019   (SI) .................................. 201900185

(51) Int. Cl.
*B05B 9/08*     (2006.01)
*A45D 34/04*    (2006.01)
(Continued)

(52) U.S. Cl.
CPC ............ *B05B 9/0861* (2013.01); *A45D 34/04* (2013.01); *A61L 9/14* (2013.01); *B05B 9/0406* (2013.01);
(Continued)

(58) Field of Classification Search
CPC ..... B05B 9/0861; B05B 9/0406; B05B 12/14; B05B 7/0408; B05B 12/1418;
(Continued)

(56) References Cited

U.S. PATENT DOCUMENTS

| 4,902,281 A | 2/1990 | Avoy |
| 5,565,241 A * | 10/1996 | Mathias ................ B05B 7/1431 |
| | | 239/296 |

(Continued)

FOREIGN PATENT DOCUMENTS

| AU | 2018268346 B2 | 10/2021 |
| CN | 201550799 U | 8/2010 |

(Continued)

OTHER PUBLICATIONS

PCT International Search Report and Written Opinion, Application No. PCT/GB2020/051569, dated Sep. 18, 2020.

(Continued)

*Primary Examiner* — Bob Zadeh
(74) *Attorney, Agent, or Firm* — MacMillan, Sobanski & Todd, LLC

(57) ABSTRACT

The present invention relates to a perfume dispensing device, the device being electronically controlled and the actuation of perfume spraying being performed via an actuator (12) located on or under a device housing (1). All components of the device are located on or in the housing (1), wherein the housing also accommodates a control circuit (10) for controlling the device, which may optionally include a system (13) for wireless communication with a smart device (14) having a dedicated application uploaded, through which the user sets the desired parameters. The device may include several storage containers (2), which allows the user to select the desired perfume or to personalise the perfume via a dedicated application. The actuator is actuated by pressing or touching the actuator (12) or via an external device.

16 Claims, 2 Drawing Sheets

Figure 1:
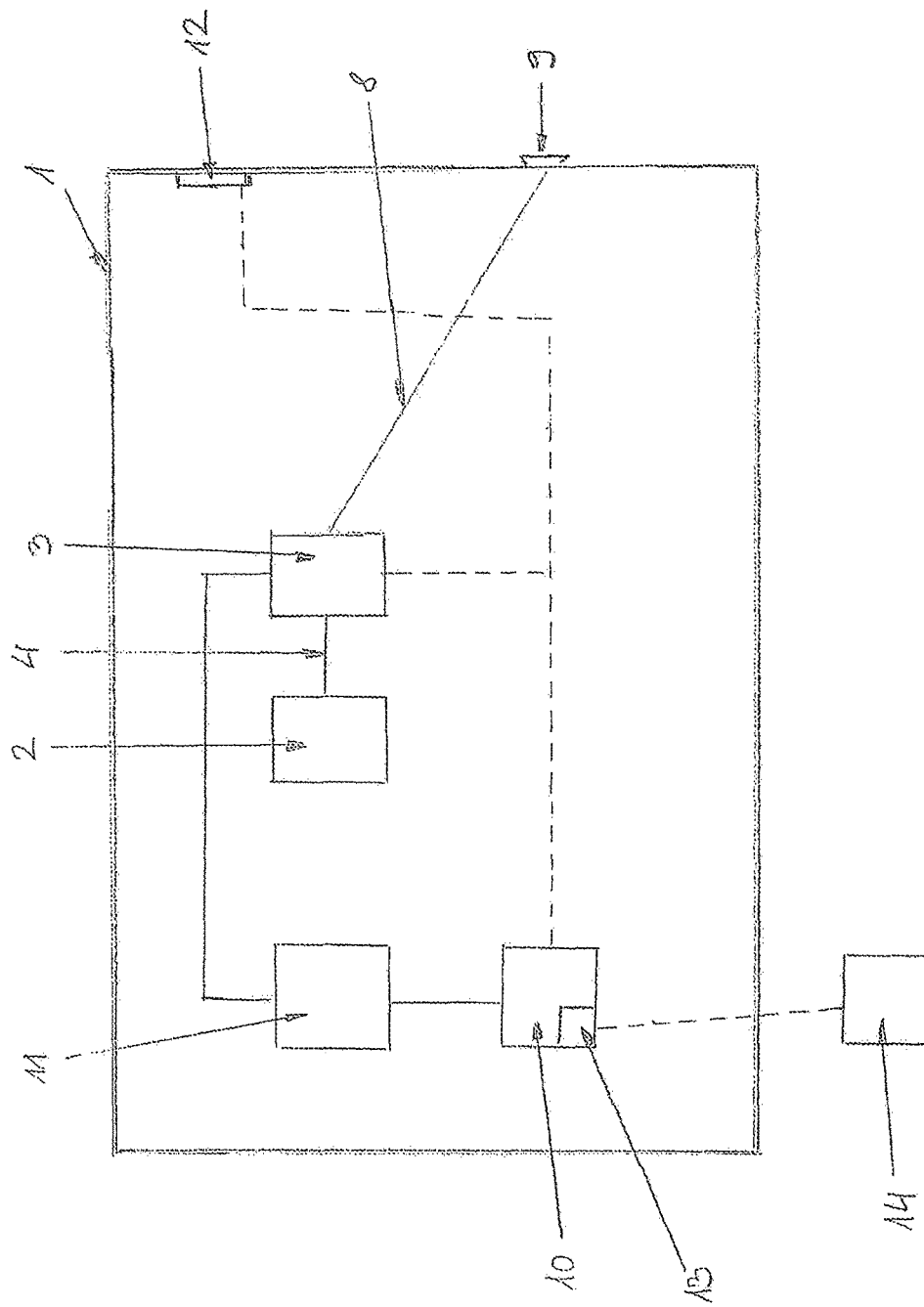

(51) Int. Cl.
  *A61L 9/14* (2006.01)
  *B05B 9/04* (2006.01)
  *B05B 12/14* (2006.01)
  *B05B 7/04* (2006.01)

(52) U.S. Cl.
  CPC .......... *B05B 12/14* (2013.01); *A45D 2200/05* (2013.01); *A45D 2200/057* (2013.01); *A61L 2209/11* (2013.01); *A61L 2209/134* (2013.01); *B05B 7/0408* (2013.01); *B05B 12/1418* (2013.01)

(58) Field of Classification Search
  CPC ... B05B 9/0811; B05B 12/00; B05B 12/1409; A45D 34/04; A45D 2200/05; A45D 2200/057; A61L 9/14; A61L 2209/11; A61L 2209/134; A61L 9/125
  See application file for complete search history.

(56) References Cited

U.S. PATENT DOCUMENTS

| | | | | |
|---|---|---|---|---|
| 5,642,761 | A * | 7/1997 | Holbrook | B67D 1/1293 141/50 |
| 5,803,320 | A * | 9/1998 | Cutting | B67D 1/0871 222/129.1 |
| 7,147,131 | B2 * | 12/2006 | Sher | B67D 1/005 222/1 |
| 10,252,904 | B2 * | 4/2019 | Bertness | B67D 7/78 |
| 10,562,757 | B2 * | 2/2020 | Biasi | G01F 3/20 |
| 10,905,163 | B2 * | 2/2021 | Manca | H05B 1/0244 |
| 2010/0205732 | A1 | 8/2010 | Muelhausen et al. | |
| 2012/0160874 | A1 | 6/2012 | De Rosa et al. | |
| 2012/0279990 | A1 | 11/2012 | Werner et al. | |
| 2016/0262457 | A1 * | 9/2016 | Borkovec | A61M 15/002 |
| 2017/0333590 | A1 | 11/2017 | Bush et al. | |
| 2017/0333922 | A1 * | 11/2017 | Selby | A61M 11/00 |
| 2020/0178671 | A1 * | 6/2020 | Edwards | B05B 11/1047 |
| 2022/0339650 | A1 * | 10/2022 | Mohorovic | A61L 9/125 |

FOREIGN PATENT DOCUMENTS

| | | |
|---|---|---|
| CN | 206363129 U | 7/2017 |
| CN | 207951784 U | 10/2018 |
| EP | 0661101 A1 | 7/1995 |
| EP | 3167712 A1 | 5/2017 |
| FR | 2772245 A1 | 6/1999 |
| GB | 1122519 A | 8/1968 |
| JP | H1047525 A | 2/1998 |
| JP | 2013503789 A | 2/2013 |
| JP | 2020520779 A | 7/2020 |
| JP | 2020521554 A | 7/2020 |
| WO | 9604997 A1 | 2/1996 |
| WO | 2016075433 A1 | 5/2016 |
| WO | 2018211253 A1 | 11/2018 |
| WO | 2018216024 A1 | 11/2018 |
| WO | 2020161310 A1 | 8/2020 |
| WO | 2020217073 A1 | 10/2020 |
| WO | 2020260906 A1 | 12/2020 |
| WO | 2021061056 A1 | 4/2021 |

OTHER PUBLICATIONS

PCT International Search Report and Written Opinion, Application No. PCT/GB2020/051049, dated Sep. 18, 2020.
PCT International Search Report and Written Opinion, Application No. PCT/SI2020/050020, dated Dec. 18, 2020.
PCT Third Party Observation, Application No. PCT/SI2020/050020, dated Apr. 21, 2021.
Chinese Search Report, Application No. 2020800676821, dated Sep. 2, 2023, translation only.
Japanese Notice of Refusal, Application No. 2022-519285, dated Jul. 6, 2024.
Japanese Search Report, Application No. 2022-519285, dated Jul. 18, 2024.
United Arab Emirates Ministry of Economy Search Report, Application No. P6000521/2022, dated Jun. 26, 2024.

* cited by examiner

PERFUME DOSING DEVICE

The present invention relates to a perfume dosing/dispensing device, the device being electronically controlled and the actuation of perfume spraying being performed via an actuator located on or under a device housing and being touch-activated. All components of the device are located on or in the housing, wherein the housing also accommodates a control circuit for controlling the device, which may optionally include a system for wireless communication with a smart device having a dedicated application uploaded, through which the user sets the desired parameters.

Said construction of the device and the electronic control allow for any design of the housing and the location of the actuator and the spray head with a spray nozzle in any place on or in the housing. Electronically controlled devices and the use of a dedicated application allow the user to use the perfume based on his wishes, i.e. personalisation of perfumes.

From prior art, perfuming devices are known, which usually consist of a bottle containing a perfume and an actuator with a spray nozzle, which is usually located on the bottle neck. To initiate spraying, the user must press the actuator with sufficient force, which can pose a problem for a weaker population, such as older people and children, and wherein the bottle and the actuator must generally be in a vertical position if the spray is to be uniform. Additionally, the actuator must be designed in a way to have the area pressed by the user, when actuating it with a finger, large enough to prevent the finger from slipping. All of the above presents limitations on the possibilities for designing perfume bottles.

The prior art devices do not allow the user to precisely control the amount of perfume that is dispensed at a single press of the actuator, i.e. to dispense a specific and always the same amount of perfume each time. The user can control the time of spraying, the power of the individual press and thus the amount of perfume to be sprayed at a single press of the actuator only by applying differently long presses on the actuator, which means that a larger amount of perfume is sprayed one time and a smaller amount at another time. Because each perfume is in its own bottle, it is not possible to prepare a personalised perfume blend, as the user can only use one perfume at a time.

Known prior art devices also do not enable instant adjustments of the device now possible by electronically controllable device, and do not enable perfume personalisation by mixing individual components or ingredients of the perfume in such a way that the user would determine the quantities of individual components of the perfume, such as, inter alia, essential oil, alcohol . . . ), which will be dispensed from individual storage containers. This allows the user to prepare an appropriate perfume according to his skin type (PH, humidity, oiliness . . . ).

Figure 2:
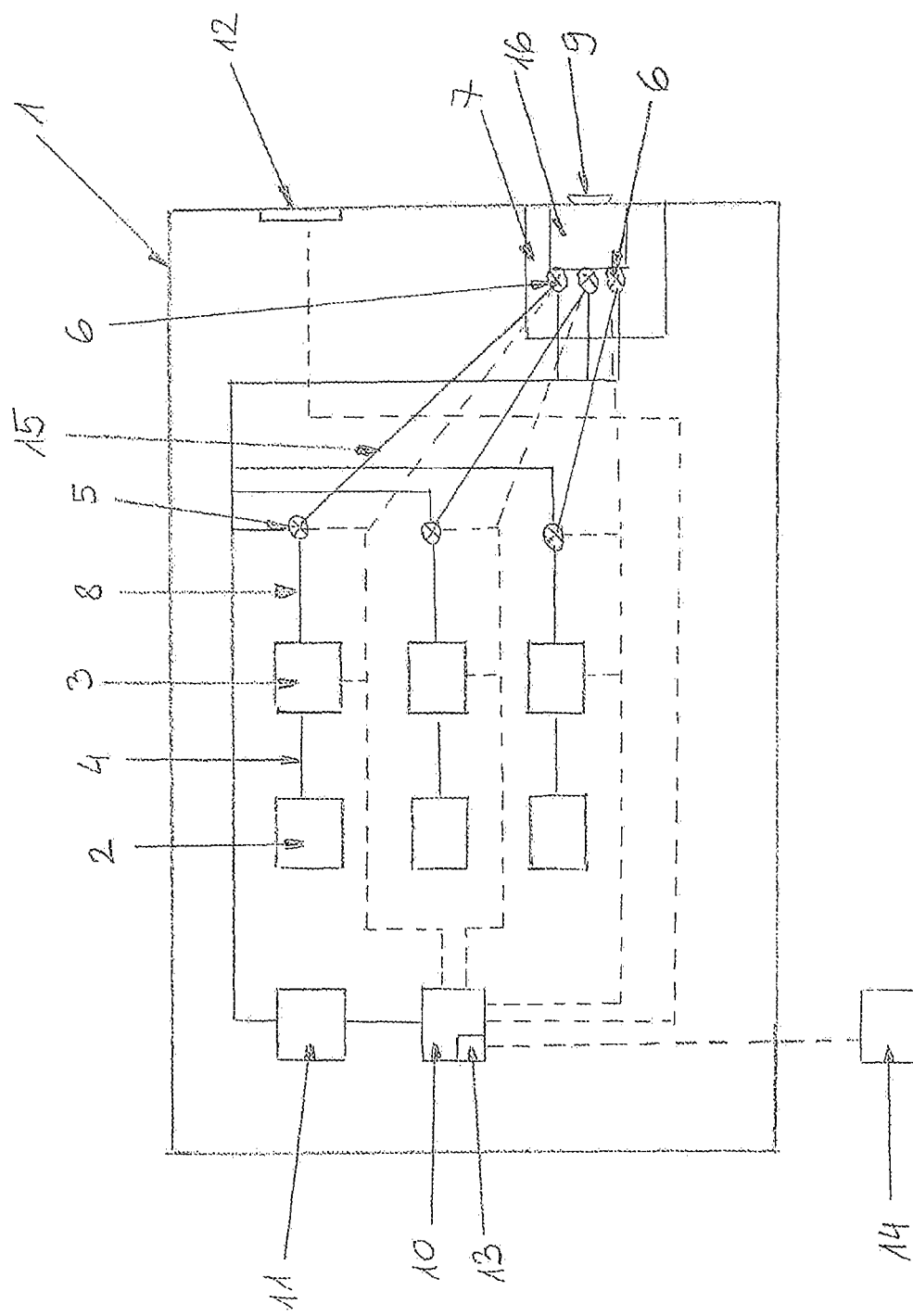

The indicated disadvantages are eliminated by a perfume dispensing device that is described herein below and represented in the figures, in which:

FIG. 1 shows an embodiment of a device of the invention with one perfume storage container FIG. 2 shows an embodiment of a device of the invention with three perfume storage containers.

A perfume dispensing device of the invention includes a housing 1 accommodating at least one liquid storage container 2;
at least one pump 3, a respective pump 3 being connected to a respective storage container 2 via a suction tube 4 and a respective pump 3 being connected with at least one spray nozzle 9 via a push tube 8;
at least one spray nozzle 9;
a control circuit 10 for controlling the device, the control circuit 10 being adapted to control at least one pump 3;
a power supply unit 11 for supplying all electronic components of the device, an actuator 12 for actuating the device being located on the housing 1, said actuator being actuated by touch or in other ways enabling the activation of the control circuit 10, and thereby through the control circuit 10 actuating at least one pump 3 which pushes a certain amount of liquid from the storage container 2 via the suction tube 4 along the push tube 8 to the spray nozzle 9 and through the spray nozzle 9 into the air.

The control circuit 10 optionally includes a communication unit 13 for wireless communication with an external device 14, which has a dedicated application uploaded, through which the user controls the device, particularly can select and set at least the following parameters:

spray power, volume and time
setting the mode of unlocking and locking the actuator 12, for example with an adequate code
insight into the status of the perfume, such as the shelf life and the amount of perfume in a respective storage container 2
setting a warning for the recommended next use with a light and/or vibrating signal
checking the originality of the perfume (that the perfume is not a counterfeit).

The external device 14 can be a smart phone or a tablet or a screen and an appropriate smart device embedded into the housing of the device.

The actuator 12 can be actuated by pressing or touching the actuator 12 or via the external device 14.

The pump 3 is electronically controlled and generates an adequate force to push the liquid out of the storage container 2 through the spray nozzle 9 by means of electricity and/or by means of compressed air, for instance a diaphragm pump.

The power supply unit 11 for supplying all electronic components of the device is preferably a battery and/or a battery pack.

The liquid contained in a respective storage container 2 is either a single perfume or a part of a perfume ingredient.

In a first embodiment shown in FIG. 1, the device includes one storage container 2, the liquid contained in the storage container 2 being a perfume. By actuating the actuator 12, the user activates the control circuit 10 which actuates the pump 3 which pushes the perfume through a system of tubes 4, 8 for the delivery of the perfume from the storage container 2 to the spray nozzle 9 and the perfume is sprayed into the room through the spray nozzle 9.

In a second embodiment shown in FIG. 2, the device of the invention includes several storage containers 2, a respective liquid contained in a respective storage container 2 being either a respective perfume or a respective perfume ingredient. In this case, the device further includes dosing valves 5 and a spray head 7 with at least one spray nozzle 9, wherein the spray head 7 further includes non-return valves 6, wherein the number of dosing valves 5 and non-return valves 6 is equal to the number of storage containers 2. Each storage container 2 has its own pump 3 and a separate system of tubes 4, 8 for the delivery of a respective liquid from a respective storage container 2 through a corresponding dosing valve 5 to the spray head 7. Each non-return valve 6 is connected with a corresponding dosing valve 5 via a separate tube 15. After use, i.e. after the device has been actuated, i.e. after spraying, the non-return valve 6 prevents the minimum amounts of a respective liquid from remaining in the spray head 7. The control circuit 10 is here further adapted also for the control of the dosing valves 5 and the non-return valves 6.

In this embodiment, the user has several options, namely the selection of an individual perfume to be dispensed from the selected storage container 2, the selection of a combination of several perfumes from the selected storage containers 2 to be dispensed from the selected storage containers 2, and the selection to individually determine the quantities of respective perfume components to be dispensed from the selected storage containers 2.

When the user wishes to dispense an individual perfume from a selected storage container 2, the user uses the dedicated application to select the desired perfume or the desired storage container 2, by actuating the actuator 12 he activates the control circuit 10 which actuates the selected pump 3 and opens the corresponding dosing valve 5 and the corresponding non-return valve 6 in the spray head 7 which pushes the selected perfume through a system of tubes 4, 8, 15 for the delivery of the perfume from the selected storage container 2 to the spray head 7 and the selected perfume is sprayed into the room through the spray nozzle 9.

When the user wishes to use a personalised blend of various perfumes from several storage containers 2 at the same time, or perfume personalisation by mixing individual perfume ingredients, a further tank 16 is foreseen in the spray head 7 for receiving a respective liquid, i.e. a respective perfume or a respective perfume ingredient from the selected storage container 2, wherein a predetermined amount of an respective liquid from the selected storage container 2 is first metered through separate systems of pipes 4, 8, 15 for delivering a respective liquid from the selected storage container 2 via a corresponding dosing valve 5 and a corresponding non-return valve 6 into the tank 16, and then the personalised perfume blend is sprayed through the spray nozzle 9 into the room.

When the user wishes to use a personalised blend of various perfumes from several storage containers 2 at the same time, the user uses the dedicated application to determine the quantity of perfume for each perfume from a respective storage container 2, by actuating the actuator 12 he activates the control circuit 10 which actuates the selected pump 3, opens the corresponding dosing valves 5 and the corresponding non-return valves 6 in the spray head 7 which dispense the predetermined amount of the selected perfume from the selected storage container 2 through a system of tubes 4, 8, 15 for the delivery of the perfume from the storage container 2 to the tank 16 in the spray head 7, wherefrom the blend is then sprayed into the room through the spray nozzle 9.

When the user wishes to use a personalised perfume by mixing individual perfume ingredients, the user uses the dedicated application to determine the quantity of a respective perfume ingredient for each ingredient from a respective storage container 2, by actuating the actuator 12 he activates the control circuit 10 which actuates the selected pump 3, opens the corresponding dosing valves 5 and the corresponding non-return valves 6 in the spray head 7 which dispense the predetermined amount of the selected perfume ingredient from the selected storage container 2 through a system of tubes 4, 8, 15 for the delivery of the respective perfume ingredient from the storage container 2 to the tank 16 in the spray head 7, wherefrom the blend is then sprayed into the room through the spray nozzle 9.

The dedicated application through which the user controls the device allows the selection and setting of at least the following further parameters:
- selection of an individual storage container 2 and the amount of perfume to be dispensed from the selected storage container 2
- selection of several storage containers 2 at the same time and the amount of a respective perfume to be dispensed from the respective storage container 2
- selection of several storage containers 2 at the same time and the amount of a respective perfume ingredient to be dispensed from the respective storage container 2.

It is understood that the proposed dispensing device is not suitable only for dispensing perfumes, i.e. components in liquid form, but is also suitable for dispensing components in other forms, such as for example creams, gels, etc.

The invention claimed is:

1. A perfume dispensing device including a housing accommodating:
   - a plurality of pumps;
   - a plurality of liquid storage containers containing a liquid, each liquid storage container of the plurality of liquid storage containers being connected to a respective pump of the plurality of pumps via a respective separate suction tube;
   - a spray head with at least one spray nozzle;
   - a control circuit for controlling said perfume dispensing device;
   - a power supply unit for supplying all electronic components of said perfume dispensing device;
   - an actuator for actuating said perfume dispensing device, the actuator located on the housing and being actuated by pushing or touching the actuator; and
   - dosing valves, each dosing valve connected to a respective pump of the plurality of pumps via a respective separate push tube;
   - wherein the spray head further includes non-return valves for preventing minimum quantities of liquid from remaining in the spray head after each use;
   - wherein the spray head further includes a tank to receive a certain amount of the liquid via the non-return valves from a respective liquid storage container;
   - wherein the number of the dosing valves and the number of non-return valves are identical to the number of liquid storage containers and each non-return valve is connected with a corresponding dosing valve via a respective separate tube;
   - wherein the control circuit is adapted for control of the plurality of pumps, of the dosing valves, and the non-return valves; and
   - wherein by actuating said perfume dispensing device, the respective pump of the plurality of pumps, the respective dosing valve, and the respective non-return valve are actuated by the control circuit, whereby a certain amount of the liquid from the respective liquid storage container is pushed via the respective separate suction tube along the respective separate push tube and the respective separate tube to the tank of the at least one spray nozzle and through the at least one spray nozzle into air.

2. The device according to claim 1, characterized in that the liquid contained in the respective liquid storage container is either a single perfume or a part of a perfume ingredient.

3. The device according to claim 1, characterized in that the pump of the plurality of pumps is electronically controlled and generates an adequate force to push the liquid out of the respective liquid storage container through the at least one spray nozzle by means of electricity.

4. The device according to claim 1, characterized in that the control circuit includes a communication unit for wireless communication with an external device through which said perfume dispensing device can be controlled.

5. The device according to claim 4, wherein the external device has a dedicated application uploaded through which said perfume dispensing device can be controlled.

6. The device of claim 5, wherein the dedicated application controls the following parameters of the perfume dispensing device: spray power, volume, and time; and
wherein to dispense a personalized blend of various perfumes from several storage containers of the plurality of liquid storage containers at the same time, the user uses the dedicated application to determine the quantity of the respective perfume to be dispensed from the respective storage container.

7. A smart perfume dispensing device including a housing accommodating:
a plurality of pumps;
a plurality of liquid storage containers containing a liquid, each liquid storage container of the plurality of liquid storage containers being connected to a respective pump of the plurality of pumps via a respective separate suction tube, the liquid being either a single perfume or a part of a perfume ingredient;
a spray head with at least one spray nozzle;
a control circuit for controlling said perfume dispensing device and enabling wireless communication with an external smart device;
a power supply unit for supplying all electronic components of said perfume dispensing device;
an actuator for actuating said perfume dispensing device, the actuator located on the housing and being actuated by pushing or touching the actuator or via the external smart device; and
dosing valves, each dosing valve connected to a respective pump of the plurality of pumps via a respective separate push tube;
wherein the spray head further includes non-return valves for preventing minimum quantities of liquid from remaining in the spray head after each use;
wherein the spray head further includes a tank to receive a certain amount of the liquid via the non-return valves from a respective liquid storage container;
wherein the number of dosing valves and the number of non-return valves are identical to the number of liquid storage containers and each non-return valve is connected with a corresponding dosing valve via a respective separate tube;
wherein the control circuit is adapted for the control of the plurality of pumps, of the dosing valve, and the non-return valves; and
wherein by actuating said perfume dispensing device, the respective pump of the plurality of pumps, the respective dosing valve, and the respective non-return valve are actuated by the control circuit, whereby a certain amount of the liquid from the respective storage container is pushed via the respective separate suction tube along the respective separate push tube and the respective separate tube to the tank of the at least one spray nozzle and through the at least one spray nozzle into air.

8. The device according to claim 7, characterized in that the pump of the plurality of pumps is electronically controlled and generates an adequate force to push the liquid out of the respective liquid storage container through the at least one spray nozzle by means of electricity.

9. The device according to claim 7, wherein the power supply unit comprises a battery.

10. The device according to claim 7, wherein the power supply unit comprises a battery pack.

11. The device according to claim 7, characterized in that the control circuit includes a communication unit for the wireless communication with the external smart device through which said perfume dispensing device can be controlled.

12. The device according to claim 11, wherein the external smart device has a dedicated application uploaded through which said perfume dispensing device can be controlled.

13. A smart perfume dispensing device including a housing accommodating:
a plurality of liquid storage containers containing a liquid, the liquid being either a single perfume or a part of a perfume ingredient;
a plurality of electronically controlled pumps, each pump connected to a respective liquid storage container via a dedicated suction tube;
a spray head with a plurality of spray nozzles, each spray nozzle connected to a respective pump of the plurality of electronically controlled pumps via a dedicated push tube;
a control circuit for controlling dispensing of the liquid from the plurality of liquid storage containers through each spray nozzle of the plurality of spray nozzles, the control circuit configured to control operation of each pump of the plurality of electronically controlled pumps, the control until including a communication unit for enabling wireless communication with an external smart device through which a user controls the perfume dispensing device;
a power supply unit for supplying all electronic components of said perfume dispensing device; and
an actuator for actuating said perfume dispensing device;
dosing valves, each dosing valve connected to a respective pump of the plurality of electronically controlled pumps via a separate push tube;
non-return valves for preventing minimum quantities of liquid from remaining in the spray head after each use, each non-return valve connected with a corresponding dosing valve via a separate tube;
wherein the external smart device has a dedicated application uploaded through which the user controls the following parameters of the perfume dispensing device: spray power, volume, and time.

14. The device of claim 13, wherein the communication unit receives user input for controlling spray parameters.

15. The device of claim 14, wherein the spray parameters include power and volume.

16. The device of claim 13, wherein the user controls the following parameters of the perfume dispensing device via the dedicated application: unlocking and locking the actuator; and
wherein to dispense a personalized blend of various perfumes from several storage containers of the plurality of liquid storage containers at the same time, the user uses the dedicated application to determine the quantity of the respective perfume to be dispensed from the respective storage container.

* * * * *